US011150247B2

(12) United States Patent
Bollhagen et al.

(10) Patent No.: US 11,150,247 B2
(45) Date of Patent: Oct. 19, 2021

(54) METHOD FOR SEROLOGICAL DETECTION OF VIRAL ANTIGENS

(71) Applicant: Roche Diagnostics Operations, Inc., Indianapolis, IN (US)

(72) Inventors: Ralf Bollhagen, Penzberg (DE); Barbara Upmeier, Iffeldorf (DE); Toralf Zarnt, Penzberg (DE); Peter Muench, Penzberg (DE); Manfred Ginter, Wielenbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/204,580

(22) Filed: Nov. 29, 2018

(65) Prior Publication Data
US 2019/0086412 A1 Mar. 21, 2019

Related U.S. Application Data

(63) Continuation of application No. PCT/EP2017/063096, filed on May 31, 2017.

(30) Foreign Application Priority Data

May 31, 2016 (EP) .................................... 16172144

(51) Int. Cl.
*G01N 33/576* (2006.01)
*G01N 33/53* (2006.01)

(52) U.S. Cl.
CPC ..... *G01N 33/5767* (2013.01); *G01N 33/5306* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 5,061,640 A | 10/1991 | Tischer et al. | |
| 6,756,347 B1 | 6/2004 | Besse et al. | |
| 7,316,905 B1 | 1/2008 | Aoyagi et al. | |
| 7,807,838 B2 * | 10/2010 | Matthews | C07D 487/04 546/342 |
| 2009/0291892 A1 | 11/2009 | Scholz et al. | |

FOREIGN PATENT DOCUMENTS

| | | | |
|---|---|---|---|
| CN | 104497098 | | 4/2015 |
| EP | 0173295 A1 | | 3/1986 |
| EP | 0363110 A2 | | 4/1990 |
| EP | 0404097 A2 | | 12/1990 |
| EP | 0717104 A2 | | 6/1996 |
| EP | 1083428 A2 | | 3/2001 |
| EP | 1308507 A2 | | 5/2003 |
| EP | 0967484 B1 | | 5/2007 |
| EP | 1020727 B1 | | 10/2008 |
| EP | 1691198 B1 | | 10/2010 |
| EP | 2327987 A2 | | 6/2011 |
| JP | H0829427 A | | 6/1996 |
| JP | H11108932 A | | 4/1999 |
| JP | 2001-004621 A | | 1/2001 |
| JP | 0967484 | * | 5/2007 ........... G01N 33/576 |
| JP | 2327987 | * | 6/2011 ........... G01N 33/576 |
| JP | 2011137747 A | | 7/2011 |
| WO | 1993/001161 A1 | | 1/1993 |
| WO | 0007023 A1 | | 2/2000 |
| WO | 2003/000878 A2 | | 1/2003 |
| WO | 2007134252 A1 | | 11/2007 |
| WO | 2012/168003 A1 | | 12/2012 |
| WO | 2013/107633 A1 | | 7/2013 |
| WO | 2015112382 A1 | | 7/2015 |

OTHER PUBLICATIONS

Shi et al. (Journal of Virology, 2003, vol. 77, p. 4160-4168).*
Galfrè, G. and Milstein C., Preparation of Monoclonal Antibodies: Strategies and Procedures, Methods in Enzymology, 1981, pp. 3-46, vol. 73.
Holliger, Philipp et al., "Diabodies": Small bivalent and bispecific antibody fragments, Proceedings of the National Academy of Sciences USA, 1993, pp. 6444-6448, vol. 90.
Hudson, Peter J. and Souriau, Christelle, Engineered antibodies, Nature Medicine, 2003, pp. 129-134, vol. 9, No. 1.
International Search Report dated Aug. 11, 2017, in Application No. PCT/EP2017/063096, 3 pps.
Kashiwakuma, Tomiko et al., Detection of hepatitis C virus specific core protein in serum of patients by a sensitive fluorescence enzyme immunoassay (FEIA), Journal of Immunological Methods, 1996, pp. 79-89, vol. 190.
Köhler, G. and Milstein, C., Continuous cultures of fused cells secreting antibody of predefined specificity, Nature, 1975, pp. 495-497, vol. 256.
Sansonno, D. et al., Detection and quantitation of HCV core protein in single hepatocytes by means of laser capture microdissection and enzyme-linked immunosorbent assay, Journal of Viral Hepatitis, 2004, pp. 27-32, vol. 11.
Tanaka, Takeshi et al., Simple fluorescent enzyme immunoassay for detection and quantification of hepatitis C viremia, Journal of Hepatology, 1995, pp. 742-745, vol. 23.

* cited by examiner

*Primary Examiner* — Agnieszka Boesen
(74) *Attorney, Agent, or Firm* — Stinson LLP

(57) ABSTRACT

The present disclosure relates to a method for detecting a core polypeptide of a hepatitis C virus (HCV) in a sample from a subject involving (a) contacting said sample with a base and with a surfactant having a cationic detergent, and (b) detecting a core polypeptide of the HCV in the sample. The present invention further relates to a method for pre-processing a sample from a subject for detection of HCV, involving contacting the sample with a base and with a surfactant having a cationic detergent; and to a pre-processing reagent for detecting HCV in a sample, having a base and a surfactant including a cationic detergent, wherein the surfactant also has a nonionic detergent. Moreover, the present disclosure further relates to kits, uses, and devices related to the methods disclosed.

14 Claims, No Drawings
Specification includes a Sequence Listing.

METHOD FOR SEROLOGICAL DETECTION OF VIRAL ANTIGENS

CROSS REFERENCE TO RELATED APPLICATIONS

This application is a continuation of International Application No. PCT/EP2017/063096 filed May 31, 2017, which claims priority to European Application No. 16172144.4 filed May 31, 2016, the disclosures of which are hereby incorporated by reference in their entirety.

SUMMARY OF THE INVENTION

The present invention relates to a method for detecting a core polypeptide of a hepatitis C virus (HCV) in a sample from a subject comprising (a) contacting said sample with a base and with a surfactant comprising a cationic detergent, and (b) detecting a core polypeptide of said HCV in said sample. The present invention further relates to a method for pre-processing a sample from a subject for detection of HCV, comprising contacting said sample with a base and with a surfactant comprising a cationic detergent; and to a pre-processing reagent for detecting HCV in a sample, comprising a base and a surfactant comprising a cationic detergent, wherein said surfactant further comprises a non-ionic detergent. Moreover, the present invention further relates to kits, uses, and devices related to the methods of the present invention.

BACKGROUND OF THE INVENTION

Hepatitis C viruses (HCV) are small, enveloped viruses of the family Flaviviridae, genus *Hepacivirus*, comprising a +-strand, single-stranded RNA as a genome. In the HCV particle, the core protein is associated with the RNA genome, forming a capsid-like structure, which is surrounded by a membrane comprising the viral glycoproteins E1 and E2. The HCV comprise at least six or seven genotypes and were identified as the causative agents of Hepatitis C, also known as non-A-non-B hepatitis.

Diagnosis of HCV infection is usually performed in blood-derived samples, typically immunologically detecting the viral core protein or detecting anti-HCV antibodies, or both, or detecting the viral genome by PCR. A generally important aspect in immunoassays for detecting HCV and in particular for detecting HCV core polypeptide is the provision of a highly sensitive and highly specific test that reliably detects infected samples in all phases after infection while the number of false results, like e.g. false positives, should remain as small as possible. In addition, susceptibility to interference is also undesirable as this often leads to unclear or false results that make further expensive and time-consuming investigation necessary. The immunological methods used in the art include various combinations of acidic or neutral treatments in the presence of detergents and/or chaotropic agents (EP 0 967 484 A1, EP 1 020 727 A1, EP 1 691 198 A1), or treating a sample or virus pelleted therefrom with chaotropic agents at alkaline pH (JP 1999178174A; EP 2 327 987 A2; Tanaka et al. (1995), J Hepatol 23: 742), aimed at disassembling viral particles in order to increase sensitivity of the assay. High salt concentrations were also used, for the same purpose (EP 1 083 428 A2). However, acid treatment causes a reversible denaturation, which may allow at least partial re-assembly of viral particles. Moreover, potentially confounding immunoglobulins from the blood sample may renature as well and, thus, are not effectively removed.

It is therefore an objective of the present invention to provide improved means and methods for detecting HCV avoiding at least in part the drawbacks of the prior art in particular with regard to increasing specificity and/or to decreasing susceptibility to interferences.

DETAILED DESCRIPTION OF THE INVENTION

This problem is solved by the means and methods of the present invention, with the features of the independent claims. Preferred embodiments, which might be realized in an isolated fashion or in any arbitrary combination are listed in the dependent claims.

Accordingly, the present invention relates to a method for detecting a core polypeptide of a hepatitis C virus (HCV) in a sample from a subject comprising
(a) contacting said sample with a base and with a surfactant comprising a cationic detergent, and
(b) detecting a core polypeptide of said HCV in said sample.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, in an embodiment relates to the indicated value ±20%.

The method for detecting a core polypeptide of a HCV of the present invention, in an embodiment, is an in vitro method. Moreover, it may comprise steps in addition to those explicitly mentioned above. For example, further steps may relate, e.g., to obtaining a sample for step a), or calculating a measurement value or a corrected measurement value in step b). Moreover, one or more of said steps may be performed by automated equipment.

Thus, in an embodiment, the method for detecting a core polypeptide of a HCV comprises the following steps:

(a) contacting a sample with a base thereby creating a reaction mixture allowing the sample to interact with said base,
(b) contacting said sample with a cationic detergent and, optionally, neutralizing said reaction mixture,
(c) adding at least two binding compounds specifically binding to said core polypeptide, at least one of said at least two binding compounds being a capture compound and at least one of said at least two binding compounds being a detector compound,
(d) forming an immunoreaction admixture by admixing said reaction mixture with said binding compounds,
(e) maintaining said immunoreaction admixture for a time period sufficient for allowing said core polypeptide present in said sample to immunoreact with the at least two binding compounds to form an immunoreaction product, and
(f) detecting the presence and/or the concentration of any of said immunoreaction product.

As will be understood by the skilled person, detecting a core polypeptide of a virus in a sample of a subject will usually be indicative of the presence of a virus. Accordingly, the method for detecting a core polypeptide of a HCV, in an embodiment, is a method for detecting a HCV in a sample from a subject comprising
(a) contacting said sample with a base and with a cationic detergent,
(b) detecting a core polypeptide of said HCV in said sample, and, thereby,
(c) detecting said HCV.

In an embodiment, in the aforementioned methods the core polypeptide is detected by a non-size discriminatory detection method, i.e., in an embodiment, a method detecting a feature of said core polypeptide without detecting the molecular mass of the analyte detected. Thus, in an embodiment, the aforementioned methods comprise a sandwich immunoassay, in particular a double antibody sandwich immunoassay, e.g. a sandwich ELISA or a sandwich ECLIA.

The term "virus" is understood by the skilled person. The term "hepatitis C virus" or "HCV", relates to the member of the genus hepacivirus also known to the skilled person. In an embodiment, the HCV is one of the HCV described in Smith et al. (2014), Hepatology 59(1): 318. In a further embodiment, the HCV is HCV genotype 1, in particular having a genome as specified in Genbank Acc No.: NC_004102.1 GI:22129792; is HCV genotype 2, in particular having a genome as specified in Genbank Acc No.: NC_009823.1 GI:157781212; is HCV genotype 3, in particular having a genome as specified in Genbank Acc No.: NC_009824.1 GI:157781216; is HCV genotype 4, in particular having a genome as specified in Genbank Acc No.: NC_009825.1 GI:157781208; is HCV genotype 5, in particular having a genome as specified in Genbank Acc No.: NC_009826.1 GI:157781210; is HCV genotype 6, in particular having a genome as specified in Genbank Acc No.: NC_009827.1 GI:157781214, or is HCV genotype 7, in particular genotype 7a, in particular having a genome as specified in Genbank Acc No.: EF108306.2 GI:763907344. In a further embodiment, the HCV is HCV genotype 1, in particular having a genome as specified in Genbank Acc No.: NC_004102.1 GI:22129792.

The term "contacting", as used in the context of the methods of the present invention, is understood by the skilled person. In an embodiment, the term relates to bringing a compound, in particular a base, of the present invention in physical contact with a sample or with a further compound and thereby allowing the compound and the further compound to interact. In an embodiment, the term "contacting a sample with a base" relates to contacting a sample as specified herein with a base, i.e. to contacting a sample or a sample diluted with a diluent with a base, wherein said diluent does not comprise a base as specified herein. Accordingly, in an embodiment, obtaining a pellet from a sample by centrifugation, optionally preceded by a precipitation step, and contacting said pellet with a base, is not contacting a sample with a base according to the present invention. As used herein, the term "reaction mixture" relates to any mixture contacting a first compound with a second compound, e.g. a base with a sample, allowing said first and second compound to react.

The term "base", as used herein, relates to a compound inducing an increase in pH in an aqueous solution. In an embodiment, the base is a Brønsted-Lowry base. In a further embodiment, the base is a compound comprising or generating hydroxide ions in an aqueous solution. In a further embodiment, the base is an alkali metal hydroxide e.g. LiOH, NaOH, KOH, or RbOH; or an alkaline earth metal hydroxide, e.g. $Be(OH)_2$, $Mg(OH)_2$, or $Ca(OH)_2$. In another embodiment, the base has a pKB value of at most 4, in an embodiment at most 3, in a further embodiment at most 2. In a further embodiment, the base is sodium hydroxide or potassium hydroxide, in particular is potassium hydroxide.

In an embodiment, contacting a sample with a base comprises incubating said sample at a pH of at least 10.5, in a further embodiment at a pH of at least 11.6, in a further embodiment at a pH of at least 11.75, in an embodiment at least 11.9, in a further embodiment at least 12, in a further embodiment at least 12.1. As will be understood by the skilled person, prolonged incubation at strongly alkaline pH may cause hydrolysis of polypeptides, including core polypeptides. Accordingly, in an embodiment, the sample is incubated at a pH of at most 14, in a further embodiment at most 13.2, in a further embodiment of at most 13. In another embodiment, the sample is incubated at a pH of from 11.75 to 12.75, in an embodiment of from 11.9 to 12.6, in a further embodiment of from 12 to 12.5. In an embodiment, the pH of an aqueous solution is determined according to DIN EN ISO 10523 (April 2012). In a further embodiment, contacting a sample with a base is contacting a sample with a buffer of a pH as indicated above, in an embodiment a buffer comprising a buffer compound having at least one $pK_B$ at a pH as indicated above.

In an embodiment, contacting a sample with a base comprises contacting said sample with a, in an embodiment aqueous, solution of a base, wherein the concentration of said base in said solution is of from 0.1 mol/l to 1 mol/l, in an embodiment is of from 0.15 mol/l to 0.5 mol/l, in an embodiment is of from 0.2 mol/l to 0.3 mol/l, in an embodiment is about 0.25 mol/l, in an embodiment is 0.25 mol/l. In an embodiment, the sample and the solution of the base, are mixed in a ratio of about 2:1 (sample:base solution) in such case, in a further embodiment in a ratio of 2:1 (sample:base solution). Thus, in an embodiment, contacting a sample with a base comprises adding said base to said sample up to a final concentration of from 0.05 mol/l to 0.17 mol/l, in an embodiment of from 0.07 mol/l to 0.09 mol/l.

In an embodiment, contacting a sample with a base comprises incubating the sample in the presence of the base for at least 5 minutes, in a further embodiment at least 9 minutes. As will be understood by the skilled person, prolonged incubation at strongly alkaline pH may cause hydrolysis of polypeptides, including core polypeptides. Accordingly, in an embodiment, the sample is incubated in the presence of the base for less than two hours, in an embodiment less than one hour, in a further embodiment less than 30 min. Accordingly, in an embodiment, the sample is incubated in the presence of the base for of from 5 minutes to 60 minutes, in an embodiment of from 6 minutes to 20 minutes, in a further embodiment of from 9 minutes to 15 minutes.

Thus, in an embodiment, contacting a sample with a base comprises incubating the sample at a pH of from 11.75 to 12.75 for of from 5 minutes to 60 minutes, in an embodiment of from 6 minutes to 20 minutes, in a further embodiment of from 9 minutes to 15 minutes. In another embodiment, contacting a sample with a base comprises incubating the sample at a pH 11.9 to 12.6 for of from 5 minutes to 60 minutes, in an embodiment of from 6 minutes to 20 minutes, in a further embodiment of from 7 minutes to 15 minutes. In a further embodiment, contacting a sample with a base comprises incubating the sample at a pH of from 12 to 12.5 for of from 5 minutes to 60 minutes, in an embodiment of from 6 minutes to 20 minutes, in a further embodiment of from 9 minutes to 15 minutes.

The method for detecting a core polypeptide of the present invention further comprises contacting the sample with a surfactant, in an embodiment before, after and/or simultaneously to contacting said sample with a base. In an embodiment, the sample is contacted with said base and with said surfactant simultaneously. As will be understood by the skilled person, the term "contacting simultaneously", in an embodiment, relates to a proceeding wherein the sample is contacted with the base and with the surfactant in such a way that the sample, the base, and the surfactant are present in a common solution for at least the time of treatment of the sample with a base as specified elsewhere herein. Accordingly, simultaneous treatment shall include a case where the base is neutralized after base treatment and, formally, is no longer present. The term "surfactant", as used herein, relates to a compound or to a mixture of compounds having amphiphilic properties and lowering surface tension of a liquid comprising them. As used herein, the term "detergent" is used in a broad sense and relates to compounds or mixtures having surfactant properties. In an embodiment, the surfactant comprises a cationic detergent. Cationic detergents are known in the art and include, without limitation, quarternary ammonium detergents.

In an embodiment, the cationic detergent is a hexadecyltrimethylammonium salt, in an embodiment is hexadecyltrimethylammoniumchloride (HTAC, CAS Number 112-02-7). In a further embodiment, the surfactant further comprises a non-ionic detergent, i.e., the surfactant is a mixture of a cationic and non-ionic detergent. In an embodiment, the non-ionic detergent is an alkylglycoside, in a further embodiment an n-alkyl-glycoside, in a further embodiment an octylglycoside (n-octyl-$\beta$-D-glucoside, CAS Number 29836-26-8). In an embodiment, the surfactant consists of said cationic detergent and said non-ionic detergent.

In an embodiment, contacting the sample with a base comprises incubating said sample at a temperature of from 10° C. to 50° C., in an embodiment of from 20° C. to 45° C., in a further embodiment of from 30° C. to 40° C., in a further embodiment at a temperature of 37±3° C.

As will be understood, depending in particular on the nature of the binding compound(s) used, it may be advantageous to neutralize the base before contacting the base-treated sample with a binding compound. Thus, in an embodiment, the method comprises the further step of neutralizing the base before detecting the core polypeptide in step b). Neutralization may, however, also be unnecessary, e.g. in case the base-treated sample is strongly diluted after base treatment and/or in case the binding compound(s) used is (are) insensitive to alkaline conditions. In an embodiment, the sample is neutralized to a pH of 7±2, in an embodiment to a pH of 7±1.5, in a further embodiment to a pH of 7±1. The skilled person knows appropriate methods for neutralizing a base in an aqueous solution. In an embodiment, neutralization is accomplished by adding a buffer compound buffered at an appropriate pH, in an embodiment by adding at least one part of a 0.2 mol/l buffer, in a further embodiment a 0.2 mol/l phosphate buffer, in a further embodiment a 0.2 mol/l potassium phosphate buffer to two parts of sample/base mixture. In an embodiment, the aforesaid 0.2 mol/l buffer is having a pH of from 5.5 to 7.5, in a further embodiment of from 6 to 7, in a further embodiment about 6.5, in a further embodiment of from 6.3 to 6.5. In an embodiment, neutralization is performed before the sample is contacted to a binding compound of the present invention. In a further embodiment, the binding compound(s) of the present invention is (are) comprised in the neutralization solution used for neutralization, i.e. neutralization is performed while contacting said HCV with a binding polypeptide.

In an embodiment, polypeptides present in the sample are not removed from the sample before treating said sample with a base. In an embodiment, denatured polypeptides are not removed from the sample after alkaline treatment, in particular after neutralizing the base. In a further embodiment, denatured polypeptides are not solubilized by addition of a chaotropic agent. It is, however, envisaged by the present invention that after or during alkaline treatment a mild surfactant is added, in an embodiment a surfactant comprising one or more detergents as specified elsewhere herein is added.

As used herein, the term "detecting" refers to detecting at least one feature, in an embodiment, an immunological feature, of a core polypeptide of an HCV to be detected in the sample, qualitatively or quantitatively. A feature in accordance with the present invention, in an embodiment, is a structural feature of a core polypeptide facilitating detection of the core polypeptide in a sample, e.g. by means of a binding compound specifically binding to said feature. In an embodiment, said feature facilitates identification, in a further embodiment quantification, of the core polypeptide by immunological means. Typical usable features are features facilitating differentiation of said core polypeptide from other chemical compounds present in a sample. In an embodiment, detecting a core polypeptide is establishing whether a core polypeptide is present or absent in the sample at a titer above the detection limit of the method. Methods of establishing a detection limit for a given method are known to the skilled person and include, e.g. dilution titration experiments. In a further embodiment, detecting is detecting semi-quantitatively or quantitatively the amount or titer of a core polypeptide or HCV in a sample. For quantitative detection, either the absolute or precise amount of the core polypeptide or HCV will be detected or the relative amount of the core polypeptide or HCV will be detected. The relative amount may be detected in a case were the precise amount can or shall not be detected. In said case, it can be detected whether the amount in which the core polypeptide or HCV is present is increased or diminished with respect to a second sample comprising said core polypeptide or HCV in a second, in an embodiment predetermined, amount.

As will be understood by the skilled person, the method of detecting the core polypeptide will depend on the assay format chosen. In an embodiment, the assay is a sandwich assay wherein an analyte, e.g. a HCV, a capsomer thereof, or a core polypeptide thereof, is bound to a capture compound bound to a solid surface, and wherein the amount of analyte captured is detected by binding of a detector compound as specified herein below to said captured analyte. In an embodiment, the capture and/or detector compound is an antibody and the sandwich assay is a sandwich immunoassay. As will be understood by the skilled person, in an embodiment, a detectable feature of the analyte may be present on the analyte more than once; in such case, the capture compound and the detector compound may both recognize said feature; or the capture compound recognizes a first feature and the detector compound recognizes a second, i.e., structurally different, feature. However, a specific detectable feature of the analyte may be present on the analyte only once; in such case, in an embodiment, the capture compound recognizes a first feature and the detector compound recognizes a second, i.e., structurally different, feature.

In an embodiment, the feature of the HCV and/or of the core polypeptide detected is an epitope comprised in a core polypeptide of said HCV. The term "core polypeptide", in the context of HCV, is known to the skilled person as relating to the polypeptide binding to the viral RNA in the viral particle; for this reason, the core polypeptide is also referred to as "capsid polypeptide" or "capsid protein", although HCV does not form regular capsid structures as known from most other viruses. Thus, in an embodiment, the term core polypeptide relates to the polypeptide being the major structural component of the viral core, wherein, in an embodiment, a structural component of a core is a component which is required for forming a structurally normal core and/or for forming an infectious viral particle. In a further embodiment, the core polypeptide is a polypeptide being present in a viral core in at least 5 copies per capsid or capsid-like structure, in an embodiment at least 10 copies per capsid or capsid-like structure. In a further embodiment, the core polypeptide of the HCV is the viral core polypeptide p21 or p19, in particular comprising the amino acid sequence of SEQ ID NO: 1 or 2.

The method of the present invention comprises detecting a core polypeptide of a HCV, as specified above; accordingly, the "analyte" to be detected in said method, in an embodiment, is said core polypeptide. As will be understood by the skilled person, the method may further comprise detecting further analytes, e.g. one or more further core polypeptide(s). As will be also understood by the skilled person, detecting a viral core polypeptide as an analyte, in an embodiment, may include detecting oligomers of said core polypeptide and/or may include detecting intact capsids.

In an embodiment, detecting a core polypeptide comprises contacting the sample to a binding compound. As used herein, the term "binding compound" relates to a chemical molecule binding to the analyte of the present invention, in an embodiment, to a core polypeptide. In an embodiment, the binding compound is an organic molecule or a complex thereof, in a further embodiment, a biological macromolecule, in particular a polypeptide or a complex thereof. In an embodiment, the binding compound is an antibody, in particular a monoclonal antibody. Thus, as used herein, the term "immunoreaction product" relates to a, in an embodiment specific, complex between at least one antibody and a core polypeptide of the present invention, in particular a HCV core polypeptide. In an embodiment, the binding compound binds, indirectly or directly, to the analyte of the present invention with sufficient affinity to allow detection of the complex comprising analyte and binding compound.

In an embodiment, the dissociation constant ($K_d$) of the analyte/binding compound complex is at most $10^{-7}$ mol/l, in a further embodiment, at most $10^{-8}$ mol/l, in a further embodiment, at most $10^{-9}$ mol/l. In an embodiment, the binding compound binds, indirectly or directly, to the core polypeptide of the present invention with sufficient affinity to allow detection of the complex comprising core polypeptide and binding compound. In an embodiment, the binding compound is a compound binding specifically to an analyte, in particular to a core polypeptide, of the present invention. In an embodiment, the binding compound specifically binds to (i) alkaline-treated core polypeptide or to (ii) alkaline-treated core polypeptide and non-alkaline-treated core polypeptide; thus, in an embodiment, the binding compound binds to an epitope of a core polypeptide not denatured by alkaline treatment as specified elsewhere herein. In a further embodiment, the binding compound binds to a contiguous (linear) epitope, i.e. an epitope formed by amino acids which are contiguous in the amino acid sequence of the analyte, e.g. the core polypeptide. Thus, in an embodiment, the binding compound is a binding compound not binding to a conformational epitope of the analyte. In an embodiment, the binding compound specifically binding to (i) alkaline-treated core polypeptide or to (ii) alkaline-treated core polypeptide and non-alkaline-treated core polypeptide is a binding compound identified by the method described herein below. In an embodiment, at least one binding compound binds to an epitope corresponding to amino acids 157-169 of a HCV core protein, in an embodiment corresponding to amino acids 157-169 of SEQ ID NO:1. In a further embodiment at least one binding compound binds to an epitope corresponding to amino acids 102-112 of a HCV core protein, in an embodiment corresponding to amino acids 102-112 of SEQ ID NO:1. In an embodiment, at least one binding compound binds to an epitope corresponding to amino acids 157-169 of a HCV core protein, in an embodiment corresponding to amino acids 157-169 of SEQ ID NO:1 and at least one further binding compound binds to an epitope corresponding to amino acids 102-112 of a HCV core protein, in an embodiment corresponding to amino acids 102-112 of SEQ ID NO:1.

As the skilled artisan will appreciate, the term "binding specifically", or a grammatical variation thereof, is used to indicate that other compounds, typically biomolecules, present in a sample do not significantly bind to a ligand, in particular a binding compound, of the present invention; in an embodiment, this does not exclude binding of chemical compounds, e.g. interfering compounds, to regions of the binding compounds not involved in interaction with the analyte. In an embodiment, the level of binding of a binding compound to a compound other than the analyte results in a binding affinity which is at most 10% or less, 5% or less, 2% or less, or 1% or less of the affinity to the analyte, respectively.

In an embodiment, detecting a core polypeptide comprises capturing a core polypeptide to a solid surface by means of a capture compound. As used herein, the term "capture compound" relates to a binding compound attached or adapted to be attached to a solid surface as specified elsewhere herein. As will be understood by the skilled person, the capture compound may be attached to a solid surface before, simultaneously to, or after contacting said capture compound with a sample. In an embodiment, the capture compound is attached to a solid surface simultaneously to contacting said capture compound with a sample, e.g. by mixing said sample, said capture compound, and said solid surface, which may be in the form of beads in such case. As the skilled person will understand, contacting a solid-surface bound capture compound with a sample allows for specifically separating an analyte bound by said capture compound, if present, from other compounds comprised in said sample. Methods of attaching binding compounds, e.g. biological molecules, typically polypeptides, to solid surfaces are well known in the art and include, e.g., binding by hydrophobic interaction, biotinylation and binding via immobilized streptavidin, covalent binding, antibody-antigen interaction, and the like, or a combination of these interactions. In an embodiment, the capture compound may also be a capture complex. In an embodiment, the capture compound is an antibody. In a further embodiment, the capture compound is a monoclonal antibody. In another embodiment, the capture compound is an antibody, i.e. a capture antibody, in particular a monoclonal antibody. In an embodiment, the capture antibody is covalently coupled to biotin.

In an embodiment, detecting a core polypeptide comprises contacting said core polypeptide with a detector compound. As used herein, the term "detector compound" relates to a binding compound bonded to an indicator as specified elsewhere herein. In an embodiment, the detector compound is not bound to a solid surface and not adapted to be bound to a solid surface. In an embodiment, the detector compound is a compound directly binding to the analyte of the invention, in an embodiment, to a core polypeptide. In an embodiment, the detector compound may also be a detector complex. The skilled person knows how to bond a binding compound or binding complex to an indicator, depending on the indicator selected. In an embodiment, the bond between the binding agent and the indicator in the detector compound is a covalent bond. In an embodiment, the detector compound is an antibody, i.e. a detector antibody. In a further embodiment, the detector compound is a monoclonal antibody. In another embodiment, the detector compound is an antibody, in particular a monoclonal antibody, covalently coupled to a complex comprising a Ruthenium ion, e.g. a Tris(2,2'-bipyridyl)ruthenium(II)-complex.

In an embodiment, the binding compound of the capture compound and the binding compound of the detector compound are non-identical. In an embodiment, at least one capture compound or binding compound binds to an epitope corresponding to amino acids 157-169 of a HCV core protein, in an embodiment corresponding to amino acids 157-169 of SEQ ID NO:1. In a further embodiment, at least one detector compound or binding compound binds to an epitope corresponding to amino acids 102-112 of a HCV core protein, in an embodiment corresponding to amino acids 102-112 of SEQ ID NO:1. In an embodiment, at least one capture compound binds to an epitope corresponding to amino acids 157-169 of a HCV core protein, in an embodiment corresponding to amino acids 157-169 of SEQ ID NO:1. In a further embodiment, at least one detector compound binds to an epitope corresponding to amino acids 102-112 of a HCV core protein, in an embodiment corresponding to amino acids 102-112 of SEQ ID NO:1. In an embodiment, at least one capture compounds binds to an epitope corresponding to amino acids 157-169 of a HCV core protein, in an embodiment corresponding to amino acids 157-169 of SEQ ID NO:1, and at least one detector compounds binds to an epitope corresponding to amino acids 102-112 of a HCV core protein, in an embodiment corresponding to amino acids 102-112 of SEQ ID NO:1.

The term "indicator", as used herein, relates to a compound adapted for making the presence of a molecule or complex comprising said indicator detectable. Typically, the indicator has a detectable property, typically an optical or/and enzymatic property. It is, however, also envisaged that said detectable property is the property of emitting radioactivity.

The term "optical property", as used herein, relates to any property which can be detected by an optical instrument. Specifically, the optically determinable property may be or may comprise at least one property selected from the group consisting of: a reflection property, a transmission property, an emission property, a scattering property, a fluorescence property, a phosphorescence property, a diffraction property, and a polarization property. Further optical properties envisaged by the present invention are color, fluorescence, luminescence, or refraction. In an embodiment, an optically determinable property as referred to herein refers to a property of a chemical compound which can be optically detected such as light absorption, light emission, light remission, or properties associated therewith. It will be understood that detecting an optically determinable property as used herein encompasses the detection of the presence of a property which was not detectable before, the detection of the absence of a property which has been detected before, and the detection of quantitative changes of a property, i.e., the detection of the change of the signal strength which correlates to the extent of the change of the at least one optical property. It is understood that the term "optically determinable property", in an embodiment, also relates to electro chemiluminescence, which is also known as electro-generated chemiluminescence.

The term "enzymatic property", as used herein, relates to a property of an indicator of producing a detectable product from a substrate by means of biological catalysis. Accordingly, an enzymatic property is typically conferred by the presence of a polypeptide having said enzymatic property in said indicator. Typically, the enzymatic property is at least one enzymatic activity selected from the group consisting of: phosphatase activity (e.g. in alkaline phosphatase), peroxidase activity (e.g. in horseradish peroxidase), and glycosidase activity (e.g. in beta-galactosidase). Typical substrates for enzymatic activities are well-known in the art. Typically, said enzymatic activity produces a product having a determinable optical property as specified herein above, or/and said enzymatic activity produces a product being determinable by an electrical instrument.

As used herein, the term "solid surface" relates to any suitable solid surface adapted for binding the capture compound of the present invention and adapted for being separated, e.g., by physical means, from a sample. In an embodiment, said solid surface is a surface of a bead, in an embodiment, a microbead, e.g. a magnetic or paramagnetic microbead. In an embodiment, said surface is adapted to improve binding of the capture compound, e.g. by attaching, covalently or noncovalently, molecules binding a substructure of the capture compound. Typical molecules binding a substructure of the capture compound are, e.g. antibodies, streptavidin, complexed Nickel ions, and the like. In a further embodiment, the solid surface binds said capture compound by covalent and/or non-covalent bonds, e.g. by hydrophobic interaction. Thus, in an embodiment, said solid surface is a surface of a multi-cluster plate. In an embodiment, the surface of the multicluster plate is pretreated to increase affinity and/or capacity for binding of a capture compound. Suitable pretreatments are known in the art.

The term "sample", as used herein, relates to a sample suspected to comprise HCV or constituent parts thereof of the present invention. In an embodiment, the sample is a sample suspected to comprise a core polypeptide, in particular a HCV core polypeptide, of the present invention. In an embodiment, the sample is or comprises a sample of a body fluid, a sample from a tissue or an organ, or a sample of wash/rinse fluid or a swab or smear obtained from an outer or inner body surface. In an embodiment, samples of stool, urine, saliva, cerebrospinal fluid, blood, serum, plasma, or lacrimal fluid are encompassed as samples by the method of the present invention. Samples can be obtained by use of brushes, (cotton) swabs, spatula, rinse/wash fluids, punch biopsy devices, puncture of cavities with needles or lancets, or by surgical instrumentation. However, samples obtained by well-known techniques including, in an embodiment, scrapes, swabs or biopsies from the urogenital tract, perianal regions, anal canal, the oral cavity, the upper aerodigestive tract and the epidermis are also included as samples of the present invention. Cell-free fluids may be obtained from the body fluids or the tissues or organs by lysing techniques such as homogenization and/or by separating techniques such as filtration or centrifugation. In an embodiment, samples are obtained from body fluids known to comprise HCV and/or HCV core polypeptides of the present invention, i.e., in an embodiment, blood, plasma, serum, saliva, or the like. It is to be understood that a sample may be further processed in order to carry out the method of the present invention. Particularly, cells may be removed from the sample by methods and means known in the art. In an embodiment, the sample is a sample comprising immunoglobulins, in an embodiment, a blood, serum, or plasma sample, in a further embodiment, a serum or plasma sample.

The term "subject", as used herein, relates to an animal, in an embodiment a mammal, in a further embodiment a primate, in a further embodiment a human. In an embodiment, the subject according to the present invention is a subject suspected to be infected with HCV; accordingly, in an embodiment, the subject is a subject showing at least one, in a further embodiment, at least two symptoms of HCV infection as known to the skilled person and as specified elsewhere herein. It is, however, also envisaged that the subject is a sexual partner, a family member, a household member, a fellow worker, a playfellow, and/or a custodian of a subject diagnosed to be infected with HCV.

The term "antibody", as used herein, includes monoclonal antibodies, multispecific antibodies (e.g. bispecific antibodies) formed from at least two intact antibodies, and antibody fragments so long as they exhibit the desired binding activity as specified elsewhere herein. In an embodiment, the antibody is a monoclonal antibody. In an embodiment, the antibody is a full-length antibody or an antibody fragment.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W. B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region. "Antibody fragments" comprise a portion of an intact antibody, in an embodiment, comprising the antigen-binding region thereof. Examples of antibody fragments include Fab, Fab', F(ab')2, and Fv fragments; diabodies; linear antibodies; single-chain antibody molecules, nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

The term "monoclonal antibody" as used herein refers to an antibody obtained from a population of substantially homogeneous antibodies, i.e., the individual antibodies comprised in the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds an analyte, wherein the analyte-binding polypeptide sequence was obtained by a process that includes the selection of a single analyte binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals.

In an embodiment, the method for detecting a core polypeptide of the present invention further comprises contacting said sample with further compounds. Further compounds which may be used simultaneously to treatment with a base may include, without limitation, alkali metal halogenides, in an embodiment, alkali metal chlorides, in particular potassium chloride, in an embodiment at a concentration of from 0.1 mol/l to 1 mol/l, in an embodiment, of from 0.2 mol/to 0.5 mol/l, in a further embodiment of about 0.375 mol/l, in a further embodiment of 0.375 mol/l: Moreover, in an embodiment, the method for detecting a core polypeptide of the present invention further comprises after treatment with a base contacting said sample with further compounds commonly used in detection assays, in particular immunological assays, like buffers, e.g. potassium phosphate buffers, further detergents, including anionic, non-ionic, and/or zwitterionic detergents, preservatives, polypeptides or mixtures thereof, e.g. bovine serum albumin, immunoglobulins, and the like.

In an embodiment, the method for detecting a core polypeptide of the present invention does not comprise contacting the sample with a sulfhydryl compound. In a further embodiment, the method for detecting a core polypeptide of the present invention does not comprise contacting the sample with a reducing agent. The term "sulfhydryl compound", as used herein, relates to compounds, in an embodiment organic compounds, comprising at least one —SH group, like, e.g. dithiothreitol, β-mercaptoethanol, β-mercaptoethanamine, β-mercaptoethane sulfonic acid, and the like. The term "reducing agent" is understood by the skilled person. In an embodiment, the term relates to an agent reducing —S—S— groups of polypeptides.

In a further embodiment, the method for detecting a core polypeptide of the present invention does not comprise contacting the sample with a chaotropic agent, such as urea. The term "chaotropic agent", as used herein, relates to a compound disrupting the tertiary structure of macromolecules, in particular of polypeptides. In an embodiment, according to the present invention, cationic detergents and non-ionic detergents are not chaotropic agents.

Advantageously, it was found in the work underlying the present invention that HCV core polypeptides, in particular the HCV core polypeptide, in contrast to most other polypeptides, remain soluble even after strongly alkaline treatment. Accordingly, alkaline pretreatment was found to decrease the signal of interfering compounds, thus improving the specificity of the HCV antigen assay by eliminating false-positive results.

The definitions made above apply mutatis mutandis to the following. Additional definitions and explanations made further below also apply for all embodiments described in this specification mutatis mutandis.

The present invention further relates to a method for pre-processing a sample from a subject for detection of HCV, comprising contacting said sample with a base and with a surfactant comprising a cationic detergent.

The method for pre-processing a sample from a subject may also comprise steps in addition to those explicitly mentioned. Moreover, the method, in an embodiment, is an in vitro method.

The present invention also relates to a pre-processing reagent for detecting HCV in a sample, comprising a base and a surfactant comprising a cationic detergent, wherein said surfactant further comprises a non-ionic detergent.

The term "pre-processing reagent", as used herein, relates to a solution, in an embodiment an aqueous solution, of the indicated components used to pretreat a sample before contacting said sample to a binding compound. As will be understood by the skilled person, the term "pretreatment" relates to a, typically optional, working step in a detection method, e.g. a diagnostic method of the present invention, performed before the actual detection step and aiming at improving the result of said detection step. Thus, further pretreatment steps may, e.g. relate to homogenizing a tissue sample, removing blood cells from a blood sample, and the like.

In an embodiment, as specified herein above in more detail, the base is an alkali metal or an earth alkali metal base, in an embodiment is sodium hydroxide, potassium hydroxide, or lithium hydroxide, in an embodiment is sodium hydroxide or potassium hydroxide, in a further embodiment is potassium hydroxide. Also in an embodiment, the concentration of the base in the preprocessing reagent is of from 0.1 mol/l to 1 mol/l, in an embodiment is of from 0.15 mol/l to 0.5 mol/l, in an embodiment is of from 0.2 mol/l to 0.3 mol/l, in an embodiment is about 0.25 mol/l, in an embodiment is 0.25 mol/l. Embodiments of surfactants and of detergents comprised therein have been described herein above. In an embodiment, the pre-processing reagent comprises the cationic detergent at a concentration of from 1.3% (w/v) to 2% (w/v), and said non-ionic detergent at a concentration of at least 0.25% (w/v), in an embodiment of from 0.25% (w/v) to 2.5%, in a further embodiment of from 0.3% (w/v) to 1.5% (w/v). In an embodiment, the preprocessing reagent is a threefold concentrated agent, i.e. 1 part of the pre-processing reagent is diluted with 2 parts of non-pre-processing reagent, e.g., in an embodiment, with 2 parts of sample, wherein said sample may be diluted with an appropriate diluent or, in a further embodiment, is an undiluted sample. In an embodiment, the pre-processing reagent does not comprise a compound comprising a sulfhydryl (—SH) group as specified elsewhere herein, in an embodiment does not comprise a reducing agent. In an embodiment, the pre-processing reagent comprises an alkali-metal halogenide, in an embodiment an alkali-metal chloride, in particular potassium chloride. In an embodiment, said alkali-metal halogenide is comprised in the pre-processing reagent at a concentration of from 0.5 mol/l to 2 mol/l, in an embodiment of from 1 mol/l to 1.5 mol/l, in a further embodiment of about 1.125 mol/l, in a further embodiment of 1.125 mol/l.

The present invention also relates to a kit for detecting a HCV in a sample, comprising a base and a surfactant comprising a cationic detergent, wherein said surfactant further comprises a nonionic detergent.

The term "kit", as used herein, refers to a collection of the aforementioned compounds, means or reagents of the present invention which may or may not be packaged together. The components of the kit may be comprised by separate vials (i.e. as a kit of separate parts) or, in particular the binding agents, two or more components may be provided in a single vial. Moreover, it is to be understood that the kit of the present invention, in an embodiment, is to be used for practicing the methods referred to herein above. It is, in an embodiment, envisaged that all components are provided in a ready-to-use manner for practicing the methods referred to above. Further, the kit, in an embodiment, contains instructions for carrying out said methods. The instructions can be provided by a user's manual in paper- or electronic form. In addition, the manual may comprise instructions for interpreting the results obtained when carrying out the aforementioned methods using the kit of the present invention. The kit comprises a surfactant, in an embodiment a surfactant as specified herein, in particular a surfactant comprising a cationic detergent and a non-ionic detergent. In an embodiment, the base and the surfactant are comprised in the same container, in a further embodiment in the same solution. In a further embodiment, the base comprised in the kit is comprised in a pre-processing reagent as specified herein above. In an embodiment, the kit further comprises at least two binding compounds, wherein at least one binding compound is a capture compound, and wherein at least one binding compound is a detector compound. In an embodiment, least one capture compound comprised in the kit comprises a biotin label. In another embodiment, at least one detector compound comprised in the kit comprises a ruthenium label. Also in an embodiment, the kit further comprises a neutralization means, e.g. a buffer.

Moreover, the present invention relates to a use of a composition comprising a base and a surfactant comprising a cationic detergent for pretreating a sample of a subject for use in an immunoassay for detecting HCV; and the invention relates to a use of a composition comprising a base and a surfactant comprising a cationic detergent for detecting HCV in a sample of a subject by means of an immunoassay.

As specified elsewhere herein, said uses, in an embodiment, do not comprise the use of a reducing agent and/or of a chaotropic agent for pretreating a sample or for detecting HCV.

Moreover, the present invention also relates to an analytic device for detecting a core polypeptide of HCV in a sample, comprising an analyzing unit with a sample treatment unit, said analyzing unit being adapted to perform the following steps:
(a) contacting a sample applied to said sample treatment unit with a base and a surfactant comprising a cationic detergent, and
(b) detecting a core polypeptide of said HCV in said sample.

In an embodiment, the sample treatment unit of the analyzing unit is connected to a controller unit, said controller unit being adapted to direct the steps as specified above to be performed.

The term "device", as used herein, relates to a system of means comprising at least the aforementioned means operatively linked to each other as to allow the result of the detection to be obtained. Preferred means for contacting a sample with a base and a surfactant comprising a cationic detergent and for detecting a core polypeptide are disclosed above in connection with the methods of the invention. How to link the means in an operating manner will depend on the type of means included into the device. In an embodiment, the means are comprised by a single device.

In an embodiment, the sample treatment unit comprises a receptacle for a sample. The receptacle may directly contact the sample, or may be a receptacle for a further means receiving the sample, wherein the further means may be e.g. a multi-well plate, to which a sample or a multiplicity of samples may be applied. Moreover, the sample treatment unit, in an embodiment, comprises a base and a surfactant comprising a cationic detergent, e.g. in a dry form or in a reservoir connected to a dosing means, e.g. a tubing connected to a pump. Optionally, the sample treatment unit may comprise a neutralizing means for decreasing the pH in the sample after contacting the sample to said base. In an embodiment, the sample treatment unit comprises at least one detector compound, e.g. in a dried form or in a reservoir connected to a dosing means, e.g. a tubing connected to a pump. In a further embodiment, the sample treatment unit comprises means for mixing and means for adjusting the temperature of a reaction mixture.

In an embodiment, the result of the detection may be obtained by visual inspection by the user or by performing a detection measurement on an appropriate device. In an embodiment, the analyzing unit of the device of the present invention further comprises a detection unit for detecting a core polypeptide of the present invention, in an embodiment for detecting the amount of a core polypeptide of the present invention. Means suitable as a detection unit according to the present invention are known to the skilled person and include, e.g. photometric devices. In an embodiment, the analytic device is an analytic device for electrochemical detection of an analyte and further comprises at least one electrode, in an embodiment, at least one working electrode. As will be understood by the skilled person, the analytic device may comprise additional electrodes, e.g. a counter electrode and/or a reference electrode; the analytic device may also comprise a combined counter electrode/reference electrode. Suitable electrode embodiments are known to the skilled person. In an embodiment, at least the working electrode is comprised in the sample receptacle of the device or in the further means for receiving the sample as specified above.

In an embodiment, the device of the present invention further comprises a data output unit, connected to the detection unit. The data output unit, in an embodiment, is adapted to output data obtained by the detection unit. Suitable data output units are known to the skilled person and include simple output units such as an indicator lamp or a display indicating that a core polypeptide was detected above the detection threshold. An output unit may, however, also be an interface to an evaluation device, wherein said interface may be any kind of means of transferring data, including, e.g. cable connections like USB, wireless connections like wireless LAN, bluetooth, and the like, or indirect connections such as data transfer by instant messaging, email, or the like.

In an embodiment, the device of the present invention is part of an analytic system, said analytic system further comprising an evaluation device. As will be understood by the skilled person, the evaluation device may be comprised in the same housing as the device of the invention, e.g. as an evaluation unit, or may be a separate device. In an embodiment, the evaluation device comprises a microprocessor programmed to receive output data from an output unit of the device of the present invention and to perform logical operations providing an evaluation of said output data. Evaluation of output data may comprise, e.g., correcting data for values measured in one or more control detection reaction, statistical calculations, e.g. calculating means of two or more parallel detection reactions, correcting data for dilution factors, comparing output data to reference values, compiling data in a list, and the like. In an embodiment, the evaluation device further comprises a data storage unit. In a further embodiment, said data storage unit comprises reference values, e.g. in a reference value data base. Moreover, in an embodiment, the data storage unit is adapted to store output data received from a device of the present invention, as specified above.

In an embodiment, where means for automatically detecting a core polypeptide of said virus are applied, the data obtained by said automatically operating means can be processed by, e.g., a computer program in order to establish a diagnosis (i.e. identifying a subject infected with an HCV). Typical means for detection are disclosed in connection with embodiments relating to the methods of the invention above. In such a case, the means are operatively linked in that the user of the system brings together the result of the determination of the amount and the diagnostic value thereof due to the instructions and interpretations given in a manual. The person skilled in the art will realize how to link the means without further inventive skills. Typical devices are those which can be applied without the particular knowledge of a specialized clinician, e.g., test stripes or electronic devices which merely require loading with a sample. The results may be given as output of parametric diagnostic raw data, preferably, as absolute or relative amounts. It is to be understood that these data will need interpretation by the clinician. However, also envisaged are expert system devices wherein the output comprises processed diagnostic raw data the interpretation of which does not require a specialized clinician. Further embodiments of devices comprise the analyzing units/devices (e.g., biosensors, arrays, solid supports coupled to ligands specifically recognizing the polypeptides, Plasmon surface resonance devices, NMR spectrometers, mass-spectrometers etc.) or evaluation units/devices referred to above in accordance with the methods of the invention.

The invention further discloses and proposes a computer program including computer-executable instructions for performing the method according to the present invention in one or more of the embodiments enclosed herein when the program is executed on an analytic device, computer or computer network. Specifically, the computer program may be stored on a computer-readable data carrier. Thus, specifically, one, more than one or even all of the method steps as indicated above may be performed by using a computer or a computer network, preferably by using a computer program.

The invention further discloses and proposes a computer program product having program code means, in order to perform the method according to the present invention in one or more of the embodiments enclosed herein when the program is executed on an analytic device, computer or computer network. Specifically, the program code means may be stored on a computer-readable data carrier.

Further, the invention discloses and proposes a data carrier having a data structure stored thereon, which, after loading into a computer or computer network, such as into a working memory or main memory of the computer or computer network, may execute the method according to one or more of the embodiments disclosed herein.

The invention further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a computer system or computer network, for performing the method according to one or more of the embodiments disclosed herein.

In an embodiment, referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present invention further discloses:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

Furthermore, the present invention relates to the use of a composition comprising a base and a surfactant comprising a cationic detergent for the manufacture of a device, kit, or composition for diagnosing an infection of a subject with HCV.

Summarizing the findings of the present invention, the following embodiments are particularly envisaged:

1. A method for detecting a core polypeptide of a hepatitis C virus (HCV) in a sample from a subject comprising (a) contacting said sample with a base and with a surfactant comprising a cationic detergent, and (b) detecting a core polypeptide of said HCV in said sample.

2. The method of embodiment 1, wherein said sample is contacted with said base and with said surfactant simultaneously.

3. The method of embodiment 1 or 2, wherein said method further comprises contacting said core polypeptide with a detector compound, in an embodiment with a detector antibody.

4. The method of any one of embodiments 1 to 3, wherein said detecting a core polypeptide comprises capturing at least one core polypeptide to a solid surface by means of a capture compound, in an embodiment by means of a capture antibody.

5. The method of embodiment 4, wherein said capture antibody and/or said detector antibody is a monoclonal antibody.

6. The method of any one of embodiments 3 to 5, wherein said capture compound and/or detector compound is a binding compound specifically binding to (i) alkaline-treated core polypeptide or to (ii) alkaline-treated core polypeptide and non-alkaline-treated core polypeptide.

7. The method of any one of embodiments 1 to 6, wherein said detecting said core polypeptide comprises detecting said core polypeptide in a sandwich immunoassay.

8. The method of any one of embodiments 1 to 7, wherein said sample is a sample of a body fluid, in an embodiment is a urine, saliva, cerebrospinal fluid, blood, serum, or plasma sample.

9. The method of any one of embodiments 1 to 8, wherein said sample is a sample comprising immunoglobulins, in an embodiment a blood, serum, or plasma sample.

10. The method of any one of embodiments 1 to 9, wherein said base is a Brønsted-Lowry base, in an embodiment is a compound comprising or generating additional hydroxide ions in an aqueous solution, in a further embodiment, is an alkali metal hydroxide or an alkaline earth metal hydroxide.

11. The method of any one of embodiments 1 to 10, wherein said base has a pKB value of at most 4, in an embodiment at most 3, in a further embodiment at most 2.

12. The method of any one of embodiments 1 to 11, wherein said base is sodium hydroxide, potassium hydroxide, or lithium hydroxide, in an embodiment is sodium hydroxide or potassium hydroxide, in a further embodiment is potassium hydroxide.

13. The method of any one of embodiments 1 to 12, wherein said contacting said sample with a base comprises adding 1 part of 0.25 mol/l solution of said base to 2 parts of said sample.

14. The method of any one of embodiments 1 to 13, wherein said contacting said sample with a base comprises incubating said sample in the presence of said base for at least 5 minutes, in an embodiment at least 9 minutes.

15. The method of any one of embodiments 1 to 14, wherein said contacting said sample with a base comprises incubating said sample at a pH of at least 11.75, in an embodiment at least 11.9, in a further embodiment at least 12, in a further embodiment at least 12.1.

16. The method of any one of embodiments 1 to 16, wherein said contacting said sample with a base comprises incubating said sample at a pH of from 11.75 to 12.75, in an embodiment of from 11.9 to 12.6, in a further embodiment of from 12 to 12.5.

17. The method of any one of embodiments 1 to 16, wherein said contacting said sample with a base comprises incubating said sample at said pH for at least 5 minutes, in an embodiment at least 9 minutes.

18. The method of any one of embodiments 1 to 17, wherein said contacting said sample with a base comprises incubating said sample at a temperature of from 10° C. to 50° C., in an embodiment of from 20° C. to 45° C., in a further embodiment of from 30° C. to 40° C., in a further embodiment at a temperature of 37±3° C.

19. The method of any one of embodiments 1 to 18, wherein said method comprises the further step of neutralizing said base before detecting said virus in step b).

20. The method of any one of embodiments 1 to 19, wherein said neutralizing comprises adding at least one part of a 0.2 mol/l buffer, in an embodiment a 0.2 mol/l phosphate buffer, to two parts of sample/base mixture.

21. The method of any one of embodiments 3 to 20, wherein said method comprises the further step of neutralizing said base before or while contacting said core polypeptide with a detector compound.

22. The method of any one of embodiments 1 to 21, wherein said cationic detergent is a quarternary ammonium detergent.

23. The method of embodiment 22, wherein said quarternary ammonium detergent is a hexadecyl trimethylammonium salt, in an embodiment is hexadecyl-trimethylammoniumchloride (HTAC, CAS Number 112-02-7).

24. The method of embodiment 22 or 23, wherein said surfactant further comprises a nonionic detergent, in an embodiment an alkyl-glycoside, in a further embodiment octylglycoside (noctyl-$\beta$-D-glucoside, CAS Number 29836-26-8).

25. The method of any one of embodiments 22 to 24, wherein said contacting said sample with a base and said contacting said sample with a surfactant are performed simultaneously.

26. The method of any one of embodiments 1 to 25, wherein denatured polypeptides are not removed from the sample after said further step of neutralizing said base.

27. The method of any one of embodiments 1 to 26, wherein said subject is a mammal, in an embodiment a primate, in a further embodiment a human.

28. The method of any one of embodiments 1 to 27, wherein said subject is a subject suspected to be infected with HCV.

29. The method of any one of embodiments 1 to 28, wherein said method does not comprise adding a compound having a sulfhydryl group to the sample, in an embodiment does not comprise reducing constituents of said sample.

30. The method of any one of embodiments 1 to 29, wherein said method does not comprise contacting said sample with a chaotropic agent.

31. A method for pre-processing a sample from a subject for detection of HCV, comprising contacting said sample with a base and with a surfactant comprising a cationic detergent.

32. A pre-processing reagent for detecting HCV in a sample, comprising a base and a surfactant comprising a cationic detergent, wherein said surfactant further comprises a non-ionic detergent.

33. The pre-processing reagent of embodiment 32, wherein said base is sodium hydroxide, potassium hydroxide, or lithium hydroxide, in an embodiment is sodium hydroxide or potassium hydroxide, in a further embodiment is potassium hydroxide.

34. The pre-processing reagent of embodiment 32 or 33, wherein the concentration of said base in said pre-processing reagent is of from 0.1 mol/l to 1 mol/l, in an embodiment is of from 0.15 mol/l to 0.5 mol/l, in an embodiment is of from 0.2 mol/l to 0.3 mol/l, in an embodiment is about 0.25 mol/l, in an embodiment is 0.25 mol/l.

35. The pre-processing reagent of any one of embodiments 32 to 34, wherein said preprocessing reagent comprises said cationic detergent at a concentration of from 1.3% (w/v) to 2% (w/v), and said non-ionic detergent at a concentration of at least 0.25% (w/v), in an embodiment of from 0.25% (w/v) to 2.5%, in a further embodiment of from 0.3% (w/v) to 1.5% (w/v).

36. The pre-processing reagent of any one of embodiments 32 to 35, wherein said cationic detergent is a quarternary ammonium detergent, in an embodiment is a hexadecyl-trimethylammonium salt, in an embodiment is hexadecyl-trimethylammoniumchloride (HTAC, CAS Number 112-02-7).

37. The pre-processing reagent of any one of embodiments 32 to 36, wherein said non-ionic detergent is an alkyl-glycoside, in a further embodiment octylglycoside (n-octyl-β-D-glucoside, CAS Number 29836-26-8).

38. The pre-processing reagent of any one of embodiments 32 to 37, wherein said preprocessing reagent comprises an alkali metal halogenide, in an embodiment KCl or NaCl, in a further embodiment KCl.

39. The pre-processing reagent of embodiment 38, wherein said pre-processing reagent comprises said alkali metal halogenide at a concentration of from 0.5 mol/l to 2 mol/l, in an embodiment of from 0.75 to 1.75 mol/l, in a further embodiment of from 1 mol/l to 1.25 mol/l, in a further embodiment of about 1.125 mol/l, in a further embodiment of 1.125 mol/l.

40. The pre-processing reagent of any one of embodiments 32 to 39, wherein said preprocessing reagent is a three-fold concentrated reagent.

41. The pre-processing reagent of any one of embodiments 32 to 40, wherein said preprocessing reagent does not comprise a compound comprising a sulfhydryl group, in an embodiment does not comprise a reducing agent.

42. A kit for detecting a HCV in a sample, comprising a base and a surfactant comprising a cationic detergent, wherein said surfactant further comprises a non-ionic detergent.

43. The kit of embodiment 42, wherein said kit further comprises at least one, in an embodiment at least two, binding compound(s) specifically binding to said virus.

44. The kit of embodiment 43, wherein said base and said surfactant are comprised in the same solution.

45. The kit of embodiment 42 or 43, wherein said base is comprised in a pre-processing reagent according to any one of embodiments 32 to 41.

46. The kit of any one of embodiments 42 to 45, wherein said kit comprises at least two of said binding compounds and wherein at least one binding compound is a capture compound, and wherein at least one binding compound is a detector compound.

47. The kit of any one of embodiments 42 to 46, wherein said at least one capture compound comprises a biotin label.

48. The kit of any one of embodiments 42 to 47, wherein said at least one detector compound comprises a ruthenium label.

49. The kit of any one of embodiments 42 to 48, wherein at least one binding compound is an antibody, in an embodiment a monoclonal antibody.

50. The kit of any one of embodiments 42 to 49, wherein at least one of said capture compounds and at least one of said detector compounds is an antibody, in an embodiment a monoclonal antibody.

51. The kit of any one of embodiments 42 to 50, wherein at least one of said capture compounds binds to an epitope corresponding to amino acids 157-169 of a HCV core protein, in an embodiment corresponding to amino acids 157-169 of SEQ ID NO:1, and wherein at least one of said detector compounds binds to an epitope corresponding to amino acids 102-112 of a HCV core protein, in an embodiment corresponding to amino acids 102-112 of SEQ ID NO:1.

52. The kit of any one of embodiments 42 to 51, wherein said kit further comprises a neutralization solution.

53. The kit of any one of embodiments 42 to 52, wherein at least one of said capture compound and detector compound is comprised in said neutralization solution.

54. Use of a composition comprising a base and a surfactant comprising a cationic detergent for pretreating a sample of a subject for use in an immunoassay for detecting HCV.

55. Use of a composition comprising a base and a surfactant comprising a cationic detergent for detecting HCV in a sample of a subject by means of an immunoassay.

56. An analytic device for detecting a core polypeptide of HCV in a sample, comprising an analyzing unit with a sample treatment unit, said analyzing unit being adapted to perform the following steps:
(a) contacting a sample applied to said sample treatment unit with a base and a surfactant comprising a cationic detergent, and
(b) detecting a core polypeptide of said HCV in said sample.

57. An analytic device for detecting a core polypeptide of HCV in a sample, comprising an analyzing unit with a sample treatment unit, said analyzing unit being connected to a controller unit, said controller unit being adapted to direct the following steps to be performed:
(a) contacting a sample applied to said sample treatment unit with a base and a surfactant comprising a cationic detergent, and
(b) detecting a core polypeptide of said virus in said sample.

58. An analytic system, comprising the analytic device of embodiment 56 or 57 and an evaluation device.

Further optional features and embodiments of the invention will be disclosed in more detail in the subsequent description of example embodiments, in particular in conjunction with the dependent claims. Therein, the respective optional features may be realized in an isolated fashion as well as in any arbitrary feasible combination, as the skilled person will realize. The scope of the invention is not restricted by the Examples provided.

EXAMPLES

Example 1: Methods

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements was used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a gene/protein to be expressed (e.g. full length antibody heavy chain), and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in E. coli, and
- a beta-lactamase gene which confers ampicillin resistance in E. coli.

Protein Determination

The protein concentration of purified polypeptides was determined by determining the optical density (OD) at 280 nm, using the molar extinction coefficient calculated on the basis of the amino acid sequence of the polypeptide or using the colorimetric BCA method.

Monoclonal Antibodies

Monoclonal antibodies have been prepared by standard hybridoma technology as known to the skilled person or by recombinant nucleic acid techniques.

One of the selected monoclonal antibodies was used as capture compound in the examples below and binds to the epitope aa 157-169 of the HCV core protein. A very similar epitope has already been disclosed in EP 1 308 507. As detection compound, a monoclonal antibody was chosen capable of binding to the epitope aa 102-112, an epitope related to epitopes also described in EP 0 967 484 and EP 1 308 507. For the immunization of mice, HCV core antigenic sequences of genotype 1a according to Genbank Acc. No: P26664.3 GI:130455, which discloses the complete polyprotein encoded by HCV genotype 1 were used. In particular, peptides either from amino acid 110-171 as recombinant fusion protein with Escherichia coli SlyD following the procedure disclosed in WO 03/000878 A2, US 2009/0291892 A1, WO 2013/107633 A1 was used for immunization. In an additional approach multiple peptides from amino acid 82-117 coupled to KLH (keyhole limpet hemocyanin) were used for immunization according to known methods.

Example 2: Labeling of Antibodies

Coupling of Biotin and Ruthenium Moieties, Respectively, to Antibodies:

Antibodies were obtained and purified according to state-of-the art-procedures that are fully familiar to a person skilled in the art.

Prior to its labeling, only the detection antibody was refined. It was cleaved by pepsin to obtain a F(ab')2 fragment and to eliminate the interference prone Fc fragment (the method is described by A. Johnstone and R. Thorpe in Immunochemistry in Practice, Blackwell Scientific 1987). The purified F(ab')2 fragment was further polymerized with the homobifunctional crosslinker disuccinimidyl suberate (DSS) and applied to a 5400 gel filtration chromatography to gather the optimal size of the F(ab')2 polymer (the principle is described in DE3640412).

For coupling, in general the lysine ε-amino groups of the antibodies were targeted by N-hydroxy-succinimide activated compounds. At a protein concentrations of 10 mg/ml, antibodies were reacted with N-hydroxy-succinimide activated biotinylation reagents and N-hydroxy-succinimide activated ruthenium labeling reagents, respectively. The label/protein ratio of biotinylation or ruthenium labeling reagent was 5:1 or 15:1, respectively. The reaction buffer was 50 mM potassium phosphate (pH 8.5), 150 mM KCl. The reaction was carried out at room temperature for 15 minutes and stopped by adding L-lysine to a final concentration of 10 mM. To avoid hydrolytic inactivation of the labels, the respective stock solutions were prepared in dried DMSO (Sigma-Aldrich, Germany). After the coupling reaction, unreacted free biotin/label was removed by passing the crude antibody conjugate through a gel filtration column (Superdex 200 HI Load) or by dialysis.

Example 3: Prototype Elecsys HCV Core Antigen Assay

The specificity of an Elecsys HCV core antigen prototype assay was assessed on an automated Cobas® e601 analyzer (Roche Diagnostics GmbH) with about 2500 blood donors.

Measurements were carried out in a sandwich assay format. Signal detection in the Cobas® e601 analyzer is based on electrochemiluminescense. In this sandwich assay the biotin-conjugate (i.e. the capture antibody) is immobilized on the surface of a streptavidin-coated magnetic bead. The detection-antibody bears a complexed ruthenium cation as the signaling moiety. In the presence of analyte, the ruthenium complex is bridged to the solid phase and emits light at 620 nm after excitation at the platinum electrode comprised in the measuring cell of the Cobas® e601 analyzer. The signal output is in arbitrary light units. Measurements were performed with HCV core antigen positive and negative human serum and plasma samples purchased from several sources.

The experimental HCV core antigen assay was conducted as follows. 50 μl of normal human serum, of HCV antigen positive sample or of blood donor sample and 25 μl of a detergent containing pretreatment reagent PT (200 mM potassium phosphate, pH 5.0, 1.125 M KCl, 1.5% hexadecyl trimethylammoniumchloride (HTAC), 0.5% octylglycoside) were incubated together for 9 minutes to release the antigen followed by the addition of 35 μl of 2 μg/ml capture antibody-biotin conjugate and 40 μl of 1 μg/ml detection antibody ruthenium label conjugate in the same assay buffer R1 and R2 (100 mM potassium phosphate, pH 7.0, 225 mM KCl, 0.5% sodium taurodeoxycholate, 0.3% zwittergent 3-14, 0.1% oxypyrion, 0.01% methylisothiazolinone, 0.2% bovine serum albumin, 0.2% bovine IgG, 50 μg/ml MAK33-IgG1, 50 μg/ml MAK33-F(ab')$_2$-Poly, 50 μg/ml MAK IgG2b/Fab2a-Poly). After additional 9 minutes incubation time 50 μl streptavidin-coated paramagnetic microparticles were added and incubated for further 9 minutes. Afterwards, the HCV core antigen was detected (via the electrochemiluminescent signal generated in these experiments).

The data in table 1 show the discrimination of HCV antigen positive samples and normal samples. Furthermore, all blood donor samples with signals above 1000 counts are supposed to be interfering samples.

TABLE 1

| | sample ID | counts |
|---|---|---|
| normal sample | #960064560 | 895 |
| HCV antigen positive samples | #217293 | 81'632 |
| | #205104 | 660'218 |
| | #205085 | 83'709 |
| | #205081 | 2'134'772 |
| | #9174627 | 112'996 |
| interfering samples | #62058 | 1'728 |
| | #4226531 | 1'588 |
| | #4226541 | 2'234 |
| | #5071077 | 1'721 |
| | #4684936 | 2'028 |
| | #5192030 | 1'569 |
| | #5161174 | 5'201 |
| | #4150067 | 2'123 |
| | #4149720 | 2'430 |
| | #4121275 | 3'892 |
| | #5192035 | 1'431 |
| | #5161097 | 1'526 |
| | #5186165 | 1'249 |
| | #5416694 | 1'540 |
| | #5071067 | 1'114 |
| | #4536139 | 1'728 |
| | #4684916 | 1'315 |
| | #4226681 | 1'401 |

Example 4: Elecsys HCV Core Antigen Prototype Assay with Alkaline Pretreatment The effect of sample preincubation with varying alkaline pH was assessed by using different KOH concentrations instead of potassium phosphate for PT as described in example 3. In order to optimize the immunological reaction the buffer salt concentration and the buffer pH for R1 and R2 were varied, additionally. Measurements were performed as described in example 3. The results are depicted in table 2 A and B.

KOH concentrations of 0.15 M or less are not sufficient to suppress all unspecific cross-interfering sample signals. KOH concentrations of 0.5 M or more tend to increase the background signal and matrix effects and deteriorate the assay sensitivity as the alkaline pH then can hardly be compensated by elevated buffer salt concentrations in R1 and R2. The pH during pretreatment of samples, therefore, may in particular be at least 11.6 or above 11.6. A low background signal is very important to achieve high signal to noise (S/N) ratios in HCV antigen positive samples and safeguard assay sensitivity. From the data of table 2 A/B a buffer for R1 and R2 containing 200 mM potassium phosphate at pH 6.5 or pH 6.3 and a PT containing 0.25 M KOH showed the best results.

TABLE 2 A

| R1/R2 buffer with | | 200 mM potassium phosphate, pH 6.3 | | | 400 mM potassium phosphate, pH 6.3 | | |
|---|---|---|---|---|---|---|---|
| PT: 1.125M KCl, octylgucoside + 1.5% HTAC, 0.5% | sample ID | 0.25M KOH counts | 0.5M KOH counts | 0.75M KOH counts | 0.25M KOH counts | 0.5M KOH counts | 0.75M KOH counts |
| normal sample | #960064560 | 747 | 1220 | 736 | 706 | 800 | 971 |
| HCV antigen positive samples | #217293 | 76'181 | 92'018 | 8'970 | 48'204 | 60'952 | 55'096 |
| | #205104 | 648'038 | 732'330 | 75'052 | 501'147 | 549'528 | 465'530 |
| | #205081 | 62'997 | 70'978 | 9'859 | 45'731 | 57'092 | 48'154 |
| | #205085 | 1'768'370 | 2'166'421 | 323'273 | 1'314'083 | 1'707'590 | 1'424'496 |
| | #9174627 | 114'518 | 129'658 | 13'645 | 87'463 | 104'560 | 91'628 |
| interfering samples | #62058 | 817 | 915 | 808 | 793 | 799 | 844 |
| | #5192035 | 857 | 1'137 | 1'474 | 825 | n.d. | n.d. |
| | #5161097 | 833 | 1'103 | 1'741 | n.d. | n.d. | n.d. |
| | #5186165 | 869 | 1'146 | 1'780 | 852 | n.d. | n.d. |
| | #5416694 | 846 | 859 | 1'884 | n.d. | n.d. | n.d. |
| | #5071067 | 854 | 1'006 | 1'913 | 812 | 873 | n.d. |
| resulting pH in pretreated sample | serum #960064560 | 12.2 | 12.9 | 13.2 | | | |
| | plasma #9174627 | 12.5 | 13.0 | 13.3 | | | |

TABLE 2 B

| R1/R2 buffer with | | 200 mM potassium phosphate, pH 6.5 | | | 200 mM potassium phosphate, pH 6.8 | | |
|---|---|---|---|---|---|---|---|
| PT: 1.125M KCl, octylgucoside + 1.5% HTAC, 0.5% | sample ID | 0.25M KOH counts | 0.15M KOH counts | 0.075M KOH counts | 0.25M KOH counts | 0.15M KOH counts | 0.075M KOH counts |
| normal sample | #960064560 | 676 | 747 | 804 | 780 | 839 | 979 |
| HCV antigen positive samples | #217293 | 51'202 | 56'371 | 68'191 | 73'349 | 76'760 | 84'116 |
| | #205104 | 489'799 | 417'386 | 505'255 | 520'078 | 591'947 | 636'745 |
| | #205085 | 49'622 | 48'313 | 59'910 | 60'129 | 64'842 | 74'257 |
| | #2050081 | 1'337'738 | 1'334'923 | 1'595'349 | 1'429'512 | 1'648'437 | 1'809'358 |
| | #9174627 | 88'444 | 66'327 | 72'974 | 119'389 | 100'399 | 83'832 |
| interfering samples | #62058 | 750 | 1'275 | 1'595 | 894 | 1'321 | 1'761 |
| | #5416694 | n.d. | 1'259 | 4'108 | 1'038 | 1'411 | 2'636 |
| | #4150067 | n.d. | 1'154 | 2'824 | 907 | 1'301 | 2'587 |
| | #4226681 | n.d. | 1'187 | 2'761 | 968 | 1'377 | 5'424 |
| | #5071077 | n.d. | 1'229 | 5'188 | 1'065 | 1'362 | 3'022 |
| | #5192030 | n.d. | 1'069 | 1'606 | 908 | 1'162 | 1'815 |
| resulting pH in pretreated sample | serum #960064560 | 12.2 | 11.0 | 10.1 | | | |
| | plasma #9174627 | 12.5 | 11.6 | 10.5 | | | |

Example 5: Resulting pH in Different Kinds of Plasma Samples after Alkaline Pretreatment In order to investigate the effect of anti-coagulants on the pH of human plasma samples after alkaline pretreatment 10 different kinds of plasma tubes containing human samples were used. Sample and PT (1.125 M KCl, 1.5% HTAC, 0.5% octylglucoside, 0.25 M KOH) were mixed in the same ratio 2:1 as described in the examples above and the resulting pH was determined (table 3). The resulting pH for all kinds of plasma could be found in the range from pH 11.9 to 12.3.

TABLE 3

| plasma type | PT: 1.125M KCl, 1.5% HTAC, 0.5% octylgucoside, 0.25M KOH |
|---|---|
| | resulting pH in pretreated sample |
| Na-citrate | 12.3 |
| Na-heparin | 12.0 |
| Li-heparin | 12.0 |
| $K_2$-EDTA | 11.9 |
| $K_3$-EDTA | 12.0 |
| ACDA | 12.2 |
| ACDB | 12.2 |
| CPD | 12.2 |
| CP2D | 12.1 |
| CPDA | 12.0 |

Example 6: Storage Stability of the Pretreatment Reagent

The long term storage of diagnostic reagents or kits is usually carried out at 2-8° C. After storage for a few days at this temperature for the preliminary optimal PT shown in example 3 precipitations were observed.

The optimization of the pretreatment composition is shown in table 4. The concentrations of KOH, octylglycoside and hexadecyl trimethylammoniumchloride (HTAC) were varied and assessed in the HCV Ag prototype assay with the preliminary optimal buffer for R1 and R2 containing 200 mM potassium phosphate at pH 6.5 shown in example 3. Solely conditions with increased concentrations of octylglycoside (0.75% and 1%) led to the elimination of precipitations.

Example 6: Influence of Reducing Agents During Sample Pretreatment on HCV Ag Detection The patent application EP2327987 A2 discloses the use of reducing agents in the second step of a two-step sample pretreatment reaction for the detection of HCV core antigen. The first step is carried out with a reagent consisting of an alkaline agent, a chaotropic agent and a non-ionic detergent.

By using 50 mM DTT in the PT of the Elecsys HCV core antigen prototype assay on the Cobas® e601 analyzer (leading to a comparable DTT concentration in the final pretreated sample as disclosed in EP2327987 A2) the assay sensitivity is substantially deteriorated (table 5). The assay buffer used in R1 and R2 for this experiment contained 200 mM potassium phosphate, pH 6.5, 225 mM KCl 0.5% sodium taurodeoxycholate, 0.3% zwittergent 3-14, 0.1% oxypyrion, 0.01% methylisothiazolinone, 0.2% bovine serum albumin, 0.2% bovine IgG. The PT consisted of 0.25 M KOH, 1.125 M KCl, 1.5% HTAC, 0.75% octylglucoside.

TABLE 5

| R1/R2 buffer with 200 mM potassium phosphate, pH 6.5 | | | |
|---|---|---|---|
| PT: 1.125M KCl, 1.5% HTAC, 0.75% octylgucoside, 0.25M KOH+ | | 0 mM DTT | 50 mM DTT |
| | sample ID | counts | counts |
| normal sample | #960064560 | 523 | 528 |
| HCV antigen positive samples | #217293 | 24'541 | 3'505 |
| | #205104 | 252'348 | 29'299 |
| | #205085 | 23'163 | 2'197 |
| | #205081 | 493'761 | 67'664 |
| | #9174627 | 30'386 | 5'503 |

Example 7: Influence of Surfactants on HCV Ag Detection

Experiments according to Example 4 were performed using pretreatment in the presence of 1.5% HTAC and 0.75% octylglycoside as well as in the absence of the detergent. Signal intensities and retrieval rates were determined for representative samples. As can be derived from Table 6, in the absence of detergent, only a small proportion of the signal obtained with the alkaline/detergent treatment according to Example 4 can be retrieved.

TABLE 4

| | | 200 mM potassium phosphate, pH 6.5 | | | | | | |
|---|---|---|---|---|---|---|---|---|
| R1/R2 buffer with PT: 1.125M KCl, 0.5% octylgucoside, | sample ID | 1.5% HTAC, 0.25M KOH reference counts | 1% octyl-glucoside counts | 0.75% octyl-glucoside counts | 0.2M KOH counts | 0.3M KOH counts | 1.25% HTAC counts | 1% HTAC counts |
| normal sample | #960064560 | 676 | 684 | 663 | 697 | 846 | 681 | 660 |
| HCV antigen positive samples | #217293 | 51'202 | 45'494 | 48'031 | 47'948 | 56'048 | 45'634 | 33'418 |
| | #205104 | 489'799 | 456'288 | 475'461 | 435'033 | 531'557 | 417'615 | 284'505 |
| | #205085 | 49'622 | 47'959 | 49'349 | 49'866 | 55'859 | 45'142 | 32'368 |
| | #205081 | 1'337'738 | 1'289'266 | 1'331'464 | 1'299'866 | 1'574'330 | 1'164'112 | 838'330 |
| | #9174627 | 88'444 | 80'619 | 77'131 | 81'023 | 96'285 | 68'783 | 45'928 |
| interfering samples | #62058 | 750 | 762 | 746 | 830 | 730 | 764 | 744 |
| | #5161174 | 967 | 876 | 861 | 821 | 1'406 | 837 | 839 |
| | #5186165 | 1'097 | 948 | 954 | 907 | 1'433 | 912 | 843 |
| | #5161097 | 761 | 758 | 738 | 768 | 1'149 | 738 | 689 |
| PT precipitation after 5 d at 2-8° C. | | yes | no | no | yes | yes | yes | yes |

TABLE 6

Signal retrieval after alkaline treatment in the presence and absence of detergent; re-trieval rate = signal without detergent/signal with detergent R1/R2 buffer with 200 mM potassium phosphate, pH 6.5

| | | PT: 1.125M KCl, 0.25M KOH+ | 1.5% HTAC, 0.75% octylgucoside | without detergent | retrieval |
| --- | --- | --- | --- | --- | --- |
| | sample ID | counts | counts | rate |
| normal sample | #960064560 | 707 | 808 | 114% |
| HCV antigen | #217293 | 40'939 | 980 | 2% |
| positive | #205104 | 418'533 | 6'256 | 1% |
| samples | #205085 | 43'647 | 1'276 | 3% |
| | #205081 | 1'268'478 | 28'833 | 2% |
| | #9174627 | 74'980 | 3'035 | 4% |

Example 8: Seroconversion Sensitivity of the Elecsys HCV Ag Prototype

Commercial seroconversion panels were tested to further assess and compare the sensitivity of the Elecsys HCV Ag prototype with alkaline PT (R1/R2 buffer and PT see example 4), with the PT described in example 3 (R1/R2 buffer and PT see example 3) and with the Elecsys Anti-HCV II. The Elecsys Anti-HCV II is an immunoassay which does not detect viral proteins, but detects anti-HCV antibodies that are produced as a consequence of the body's immune response after infection with HCV. For both of the HCV Ag assays a preliminary working cut-off index (COI) was chosen defined as sample signal divided by three times the signal of a normal negative sample.

Both of the Elecsys HCV Ag prototype variants are able to detect HCV core antigen in the window phase of an HCV infection, i.e. at a time point after infection when antibodies against HCV have not yet been generated by the patient's immune system, in a very comparable manner.

TABLE 7

| seroconversion ID | Elecsys Anti-HCV II COI | Elecsys HCV Ag prototype and PT as described for Table 1 | | Elecsys HCV Ag prototype with alkaline PT | |
| --- | --- | --- | --- | --- | --- |
| | | counts | COI* | counts | COI* |
| normal sample #960064560 | 1'010 | 0.33 | 839 | 0.33 | |
| PHV918_01 | 0.06 | 116'831 | 38.56 | 102'202 | 40.60 |
| PHV918_02 | 0.05 | 228'379 | 75.37 | 209'826 | 83.36 |
| PHV918_03 | 0.05 | 138'112 | 45.58 | 112'542 | 44.71 |
| PHV918_04 | 0.05 | 230'644 | 76.12 | 190'298 | 75.61 |
| PHV918_05 | 0.05 | 176'170 | 58.14 | 135'004 | 53.64 |
| PHV918_06 | 0.05 | 339'868 | 112.17 | 269'751 | 107.17 |
| PHV918_07 | 2.08 | 238'580 | 78.74 | 146'174 | 58.07 |
| PHV918_08 | 34.97 | 199'238 | 65.76 | 151'515 | 60.20 |
| Zepto6228_01 | 0.06 | 9'791 | 3.23 | 6'794 | 2.70 |
| Zepto6228_02 | 0.12 | 5'646 | 1.86 | 4'007 | 1.59 |
| Zepto6228_03 | 0.08 | 25'031 | 8.26 | 14'010 | 5.57 |
| Zepto6228_04 | 0.06 | 8'638 | 2.85 | 6'092 | 2.42 |
| Zepto6228_05 | 0.06 | 7'872 | 2.60 | 4'227 | 1.68 |
| Zepto6228_06 | 0.06 | 4'726 | 1.56 | 2'791 | 1.11 |
| Zepto6228_07 | 0.15 | 5'720 | 1.89 | 4'457 | 1.77 |
| Zepto6228_08 | 0.26 | 13'499 | 4.46 | 9'023 | 3.58 |
| Zepto6228_09 | 9.49 | 1'180 | 0.39 | 1'070 | 0.43 |
| Zepto6228_10 | 44.50 | 988 | 0.33 | 976 | 0.39 |
| Zepto6228_11 | 69.00 | 6'744 | 2.23 | 4'039 | 1.60 |
| Zepto6228_12 | 89.30 | 1'610 | 0.53 | 1'375 | 0.55 |
| Zepto9041_01 | 0.05 | 845 | 0.28 | 837 | 0.33 |
| Zepto9041_02 | 0.04 | 39'893 | 13.17 | 33'891 | 13.46 |
| Zepto9041_03 | 0.04 | 171'283 | 56.53 | 106'262 | 42.22 |
| Zepto9041_04 | 0.04 | 274'310 | 90.53 | 245'034 | 97.35 |
| Zepto9041_05 | 97.40 | 114'793 | 37.89 | 94'703 | 37.63 |
| Zepto9041_06 | 96.10 | 115'670 | 38.17 | 118'150 | 46.94 |
| Zepto9041_07 | 64.50 | 10'512 | 3.47 | 21'924 | 8.71 |
| Zepto9041_08 | 64.00 | 13'310 | 4.39 | 31'316 | 12.44 |
| Zepto9057_01 | 0.04 | 819 | 0.27 | 1'022 | 0.41 |
| Zepto9057_02 | 0.04 | 843 | 0.28 | 1'017 | 0.40 |
| Zepto9057_03 | 0.04 | 813 | 0.27 | 923 | 0.37 |
| Zepto9057_04 | 0.04 | 811 | 0.27 | 962 | 0.38 |
| Zepto9057_05 | 0.04 | 1'495 | 0.49 | 1'257 | 0.50 |
| Zepto9057_06 | 0.04 | 35'765 | 11.80 | 20'762 | 8.25 |
| Zepto9057_07 | 0.04 | 9'926 | 3.28 | 6'921 | 2.75 |
| Zepto9057_08 | 0.04 | 6'141 | 2.03 | 4'256 | 1.69 |
| Zepto9057_09 | 0.04 | 8'273 | 2.73 | 5'948 | 2.36 |
| Zepto9057_10 | 0.04 | 6'657 | 2.20 | 4'362 | 1.73 |
| Zepto9057_11 | 0.04 | 8'061 | 2.66 | 5'345 | 2.12 |

*COI = sample signal/3 · signal of normal sample

---

The invention claimed is:

1. A method for detecting a core polypeptide of a hepatitis C virus (HCV) in a sample from a subject comprising:

(a) contacting and incubating said sample with a base at a pH of at least 11.6 and with a surfactant comprising a cationic detergent, wherein said cationic detergent is a quaternary ammonium detergent, and (b) detecting said core polypeptide of said HCV in said sample.

2. The method of claim 1, wherein said surfactant further comprises a non-ionic detergent.

3. The method of claim 1, wherein said method does not comprise contacting the sample with a reducing agent.

4. The method of claim 1, wherein said method does not comprise contacting said sample with a chaotropic agent.

5. The method of claim 1, wherein said method further comprises contacting said core polypeptide with a detector compound.

6. The method of claim 1, wherein said detecting a core polypeptide comprises capturing at least one core polypeptide to a solid surface by means of a capture compound.

7. The method of claim 6, wherein said capture compound and/or detector compound is a binding compound specifically binding to (i) alkaline-treated core polypeptide or to (ii) alkaline-treated core polypeptide and non-alkaline-treated core polypeptide.

8. The method of claim 1, wherein said detecting said HCV core polypeptide comprises detecting said HCV core polypeptide in a sandwich immunoassay.

9. The method of claim 1, wherein said base is a Bronsted-Lowry base.

10. The method of claim 1, wherein said sample is contacted with said base and with said surfactant simultaneously.

11. The method of claim 1, wherein said sample is a sample comprising immunoglobulins.

12. The method of claim 2, wherein the surfactant comprises an alkyl-glycoside.

13. The method of claim 2, wherein the surfactant comprises octylglycoside (n-octyl-.beta.-D-glucoside, CAS Number 29836-26-8).

14. The method of claim 5 wherein the detector compound is comprised of an antibody.

* * * * *

SEQUENCE LISTING

<160> NUMBER OF SEQ ID NOS: 2

<210> SEQ ID NO 1
<211> LENGTH: 191
<212> TYPE: PRT
<213> ORGANISM: Hepatitis C virus

<400> SEQUENCE: 1

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

```
                                             -continued

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 2
<211> LENGTH: 177
<212> TYPE: PRT
<213> ORGANISM: Hepatitis C virus

<400> SEQUENCE: 2

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe
```